US00PP13965P39

(12) United States Plant Patent
Hambuchen et al.

(10) Patent No.: US PP13,965 P3
(45) Date of Patent: Jul. 8, 2003

(54) CREPE MYRTLE PLANT NAMED 'ROSEY CARPET'

(76) Inventors: Robert E. Hambuchen, 3 Oak Grove Dr., Conway, AR (US) 72032-4733; Betty J. Hambuchen, 3 Oak Grove Dr., Conway, AR (US) 72032-4733

( * ) Notice: Subject to any disclaimer, the term of this patent is extended or adjusted under 35 U.S.C. 154(b) by 0 days.

(21) Appl. No.: 09/982,461

(22) Filed: Oct. 17, 2001

(65) Prior Publication Data

US 2003/0074705 P1 Apr. 17, 2003

(51) Int. Cl.[7] ..... A01H 5/00
(52) U.S. Cl. ..... Plt./252
(58) Field of Search ..... Plt./252

(56) References Cited

U.S. PATENT DOCUMENTS

| | | | |
|---|---|---|---|
| PP4,255 | P | 5/1978 | Chopin |
| PP4,256 | P | 5/1978 | Chopin |
| PP5,283 | P | 9/1984 | Chopin |
| PP5,284 | P | 9/1984 | Chopin |

*Primary Examiner*—Kent Bell
(74) *Attorney, Agent, or Firm*—Christine J. Daugherty

(57) ABSTRACT

A new and distinct variety of the Lagerstroemia genus characterized by a dwarf size, profuse flower production, semi-seedless trait, extensive lateral branching, and lack of continual vertical growth after maturity.

3 Drawing Sheets

Latin name: The claimed new variety is *Lagerstroemia prostrata.*

Cultivar designation: The claimed new variety is 'Rosey Carpet'.

BACKGROUND OF THE INVENTION

Field of the Invention

The present invention relates to a new and distinct variety of crepe myrtle known by the market name as 'Rosey Carpet' and botanically known as *Lagerstroemia prostrata.* . The novel characteristics of the present invention are its profuse blooms, extended flowering season, semi-sterile trait, heavy branching and ground spreading capabilities, a plant width of 36 to 48 inches, and a low height range of 4 to 12 inches at full maturity, with substantially no vertical growth thereafter. The present invention is more fully described in the following paragraphs and illustrated in the accompanying color photographs.

BRIEF SUMMARY OF THE INVENTION

Robert E. Hambuchen first discovered the new variety in 1997. The original seed came from Okmulgee, Okla. Thereafter, Robert E. Hambuchen and Betty J. Hambuchen in Conway, Ark. asexually reproduced the new variety by means of hardwood and softwood cuttings from the original plant.

The following traits have been repeatedly observed and are determined to be basic characteristics of 'Rosey Carpet' which in combination distinguish this crepe myrtle as a new and distinct cultivar:

1. At maturity, a plant height ranging from 4 to 12 inches.
2. Rose-Pink inflorescences produced at most leaf nodes and at the terminal portion of most lateral branches.
3. Extensive networks of lateral branches.

'Rosey Carpet' has not been observed under all possible environmental conditions. The phenotype may vary with variations in environment such as temperature, light intensity, and daylength without a change in genotype. The following observations, measurements, and comparisons describe plants grown in Conway, Ark. in outdoor nursery beds under conditions that approximate those generally used in commercial practice.

Of the many commercial cultivars known to the inventor, the new variety, 'Rosey Carpet' is unique to other varieties in that 'Rosey Carpet' has very low height range. 'Rosey Carpet' also produces an extensive network of spreading or creeping branches. Furthermore, 'Rosey Carpet' produces rose-pink colored flowers at most leaf nodes and at the terminal portion of most lateral branches.

The new variety produces Rose-Pink inflorescences profusely over the entire plant. Unlike other crepe myrtle varieties known to the inventors, which produce inflorescences in a panicle formation near the terminal portion of the stem, this new variety produces rose-pink colored flowers at most leaf nodes and at the terminal portion of most lateral branches. The new variety produces extensive networks of lateral branches, each containing many inflorescences. The flower clusters located on the terminal portion of most lateral branches contain 7 to 20 flower buds and measure approximately 8 to 11 centimeters in height and 5 to 7 centimeters in width. In addition, most leaf nodes contain at least a single flower bud. Because of the extensive lateral branching of this new variety and the presence of the numerous blossoms, an appearance of a rosy pink "foam" of flowers appears over the entire mature plant.

Profuse blossoms are noted throughout the growing season. Even in the later portion of the growing season, when most crepe myrtle varieties contain an abundance of seeds and very little blooms, this new variety continues to produce blooms, including blooms at the nodes. During natural long day conditions, this variety does not produce seed. Less than 30 seeds per plant are produced during natural short day growing conditions. The new variety cannot be produced true from seed.

An interesting characteristic of the new variety of crepe myrtle is the very low height range. Fully mature plants reach a maximum height of approximately 12 inches, which produces a heavy branching and spreading crepe myrtle.

The new variety has demonstrated good winter hardiness to approximately 10° F. The new variety also exhibits a high resistance to the powdery mildew fungus.

A hardwood cutting from the new variety, marketed in a one, two, or trade gallon will produce a finished plant in approximately 12–14 months.

BRIEF DESCRIPTION OF THE DRAWINGS

The accompanying color photographic sheets show typical height, inflorescences, and foliage of a mature plant of 'Rosey Carpet'.

DETAILED BOTANICAL DESCRIPTION

Figure 1:
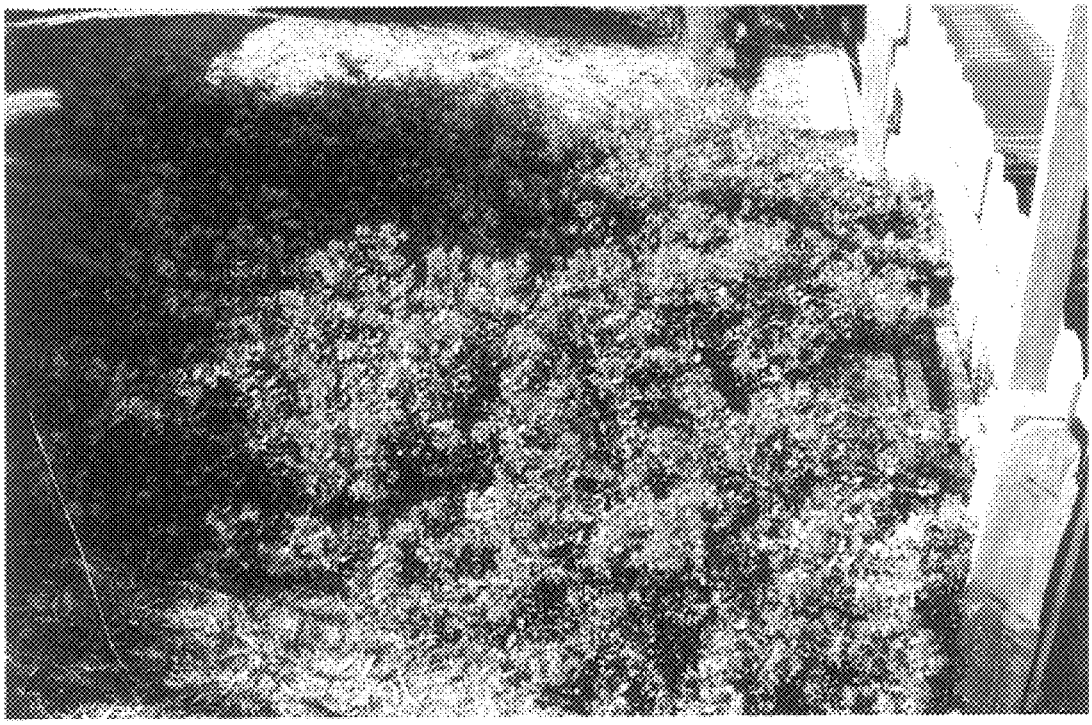
FIG. 1 is a photographic view in full color of the fully mature variety.
Figure 2:
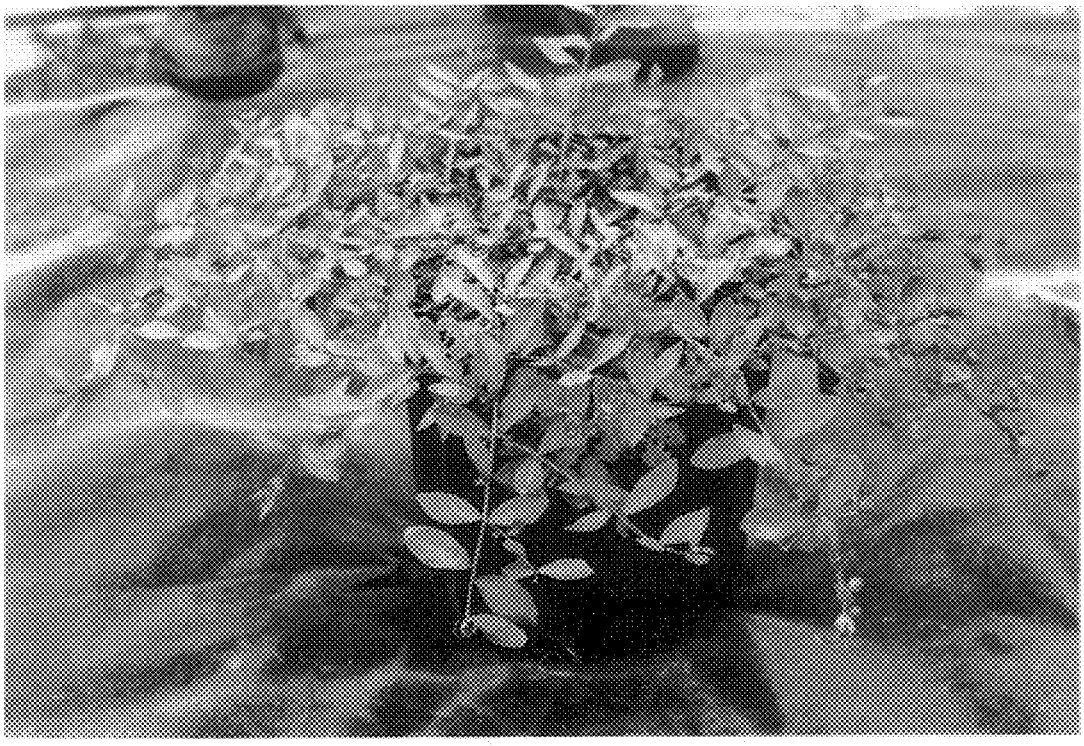
FIG. 2 is a photographic view in full color of a potted version of the variety grown for five months.
Figure 3:
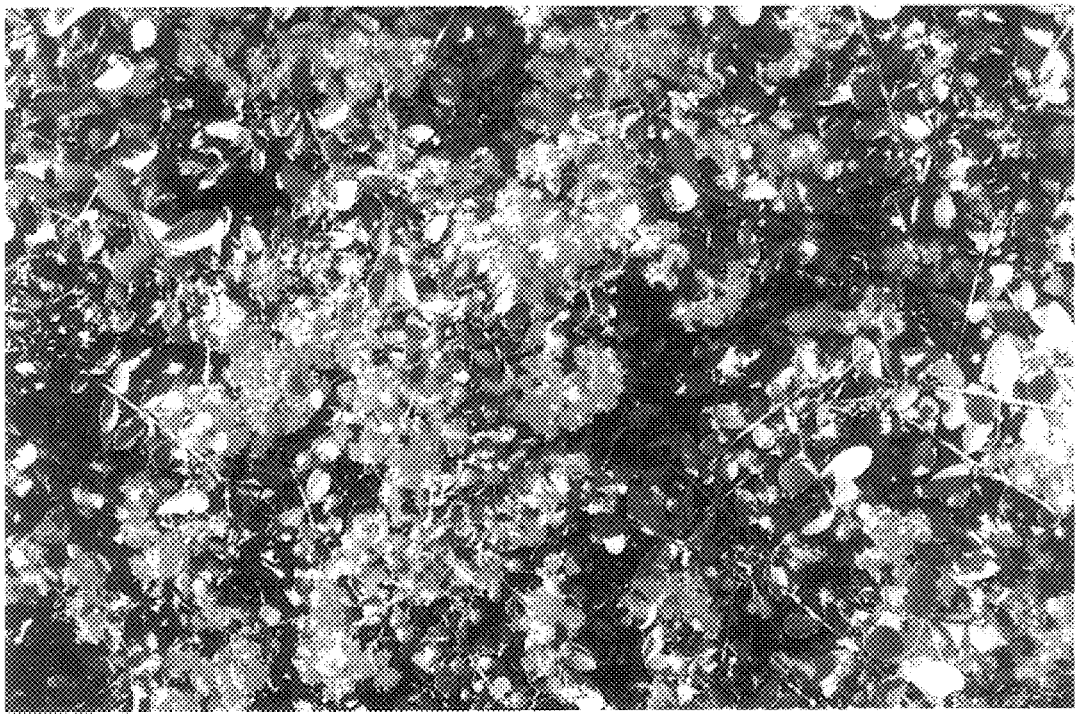
FIG. 3 is a photographic view in full color of the fully mature plant with inflorescences.

The plants described were grown in an outdoor cultivated nursery bed located in Conway, Ark. The age of the plants were approximately four years old. Observations and measurements were mainly taken during flowering. A detailed description of the new variety follows, and, to facilitate identification of the important colors, the terminology adapted by The Royal Horticultural Society Colour Chart (R.H.S.) has been followed.

Classification:

*Botanical.*—*Lagerstroemia prostrata.*

*Commerical.*—Crepe Myrtle cv. 'Rosey Carpet'.

Parentage: Original seed was obtained from an unpatented, unknown plant of Lagerstroemia from Okmulgee, Okla. Seeds from this original unknown Lagerstroemia plant were subsequently screened for low growing and spreading plants. A plant exhibiting the desired characteristics was subsequently selected. This selected plant was named 'Rosey Carpet' and was asexually propagated by softwood and hardwood cuttings.

Growth: The plant is low to the ground and compact, with a width range of 36 to 48 inches. At maturity, the plant will grow to a height ranging from 4 to 12 inches. There is substantially no vertical growth subsequent to reaching full maturity.

Branches: Multiple branches are freely produced on the young plant. The branches grow horizontally rather than vertically. Branches are gray brown, R.H.S. No. 199B, with darker stripes or streaks, R.H.S. No. 200B. Internode distances between lateral branches range from 1.5 to 2.0 centimeters. Diameters of mature branches range from 1.9 to 3.0 centimeters and have a length from 65 to 80 centimeters.

Foliage: The leaf arrangement is primarily alternate, with an occasional opposite arrangement. The leaf type is simple with pinnate venation and an entire margin. The leaf blade is ovate shape with both an acute tip and base. The leaf blade length ranges from 2 to 3 centimeters, with a width range of 1 to 1.5 centimeters. The leaf petiole is less than 1 millimeter in length and approximately light green, R.H.S. No. 138A. Mature leaves are light green, R.H.S. No. 138A on the adaxial side and yellow green, R.H.S. No. 146B on the abaxial side.

Flower: Bloom buds are red purple, R.H.S. No. 60B, turning a yellow green R.H.S. No. 145B near the pedicel. The pedicels range from 0.8 to 1.0 centimeters in length and 0.1 centimeters in width. Pedicel coloration is yellow green R.H.S. No. 145B, which then turns red purple R.H.S. No. 60B near the sepals. Six sepals appear as lobes and are approximately 1.1 to 1.3 centimeters in length and approximately 0.6 centimeters in width. Sepal coloration is approximately yellow green R.H.S. No. 145B (Both sides). The complete flowers are 2 to 3 centimeters high and have a width of 3 to 4 centimeters. Many flowers are arranged in a single bud formation located at the nodes on most stems. The flower clusters are comprised of 7 to 20 flower buds and are located at the terminal portion of most lateral branches. The flower clusters have a width of 5 to 7 centimeters and have a length of 8 to 11 centimeters. The bloom period is from June into October. The flowers have no fragrance.

Blossom: The petals are distinct and usually crumpled along the edge. Six petals comprise the blossom. An average petal length is approximately 1.2 centimeters and approximately 1 centimeter in width. An individual bloom will last for approximately 9 to 10 days. The color of the blossom is Rose Pink, R.H.S. No. 61C for both surfaces of the petals.

Reproductive organs: Stamens are formed in two whorls, with one set of filaments longer than the other. Filaments are light yellow and the anthers a darker yellow. A single pistil is produced. The style is a light green color and the stigma a red purple color. The perigynous flower consists of a superior ovary with numerous ovules. Fruit is round with a dry, hard covering. The fruit color is brown at maturity. Spontaneous seed set is seldom observed during the bloom period. During natural short-day conditions, the variety will produce a small quantity of seeds. However, because the plant is semi-sterile, few viable seeds are produced.

We claim:

1. A new distinct variety of *Lagerstroemia prostrata* plant substantially as shown and described, characterized by the distinctive Rose-Pink color blooms, profuse flower blossoms, an extended flowering period, semi-sterile trait, extensive lateral branching, a light-green colored leaf, small leaf size, a plant width of 36 to 48 inches, a height range from 4 to 12 inches, and substantially no vertical growth at full maturity.

* * * * *